(12) United States Patent
Marumoto

(10) Patent No.: US 7,050,591 B2
(45) Date of Patent: May 23, 2006

(54) ACOUSTIC OUTPUT PROCESSING APPARATUS

(75) Inventor: Toru Marumoto, Iwaki (JP)

(73) Assignee: Alpine Electronics, Inc., Tokyo (JP)

( * ) Notice: Subject to any disclaimer, the term of this patent is extended or adjusted under 35 U.S.C. 154(b) by 344 days.

(21) Appl. No.: 10/384,167

(22) Filed: Mar. 6, 2003

(65) Prior Publication Data
US 2003/0215098 A1    Nov. 20, 2003

(30) Foreign Application Priority Data
Mar. 15, 2002  (JP) .............................. 2002-073350

(51) Int. Cl.
*H04R 29/00* (2006.01)
(52) U.S. Cl. .................... 381/58; 381/98; 381/103; 381/86
(58) Field of Classification Search ................ 381/80, 381/81, 85, 123, 94.7, 86, 57, 56, 104, 107, 381/98, 103
See application file for complete search history.

(56) References Cited

U.S. PATENT DOCUMENTS 5,239,578 A     8/1993  Regen et al.
5,243,640 A  *  9/1993  Hadley et al. ............ 455/426.1
6,052,471 A  *  4/2000  Van Ryzin .................... 381/85
6,349,223 B1 *  2/2002  Chen ....................... 455/569.2
6,529,605 B1 *  3/2003  Christoph .................... 381/56

* cited by examiner

*Primary Examiner*—Brian T. Pendleton
(74) *Attorney, Agent, or Firm*—Brinks Hofer Gilson & Lione

(57) ABSTRACT

Acoustic outputs from an audio system and various acoustic output devices are produced from a speaker, and a sound which a user desires to hear clearly is automatically selected and corrected with emphasis. A TV sound, an acoustic guide of a navigation system, and a sound on the other end of a hands-free device are delivered to a selector, and one of them is selected by a selector switching control and corrected by an acoustic correction filter to be produced. The other acoustic signals are produced as non-correction target signals together with an audio signal. An acoustic output processing control unit performs operational control of acoustic output processing corresponding to an operation mode of an acoustic output device and a present mode of acoustic output processing detected by device operation-mode detecting means while performing various operational function controls, including selector switching control and buzzer control, corresponding to data obtained by reading a memory in which modes of acoustic output processing are stored in advance.

19 Claims, 5 Drawing Sheets

FIG. 2

| PRESENT EMPHASIS CORRECTION PROCESS SIGNAL | ACOUSTIC GUIDE OF NAVIGATION SYSTEM | | HANDS-FREE DEVICE | TV SOUND |
|---|---|---|---|---|
| | PRIOLITY SMALL | PRIOLITY LARGE | | |
| ACOUSTIC GUIDE OF NAVIGATION SYSTEM | | | SELECTED ITEM (1) | SELECTED ITEM (2) |
| HANDS-FREE DEVICE | SELECTED ITEM (3) | SELECTED ITEM (4) | | SELECTED ITEM (5) |
| TV SOUND | SELECTED ITEM (6) | SELECTED ITEM (7) | SELECTED ITEM (8) | |
| PRIORITY ORDER | 1 | 2 | 3 | 4 |

FIG. 3

| ITEMS | SELECTABLE PROCESS CONTENTS | REMARKS |
|---|---|---|
| SWITCHING: EMPHASIS CORRECTION | CORRECT SOUND EMPHATICALLY BY SWITCHING INTERRUPTING SIGNAL WITH PRIORITY | ACOUSTIC CORRECTION DEVICE "ON": SWITCHING COTROL-TARGET SIGNAL BY SELECTOR |
| SWITCHING: NON-EMPHASIS CORRECTION | SWITCHING INTERRUPTING SIGNAL WITH PRIORITY, CORRECT SOUND NON-EMPHATICALLY | ACOUSTIC CORRECTION DEVICE "OFF" |
| BEEP (SMALL) | URGE TO LOOK AT MONITOR WITH BEEP | UNCHANGED BEFORE INTERRUPTION |
| BEEP (LARGE) | URGE TO LOOK AT MONITOR WITH LARGE BEEP | UNCHANGED BEFORE INTERRUPTION |
| MUTE | EMPHASIZE SOUND RELATIVELY BY MUTING AUDIO | ACOUSTIC CORRECTION DEVICE "OFF": ESTABLISHED PROCESSING |
| UNCHANGED | OUTPUT AS IT IS | INTERRUPTION NOT ALLOWED |

FIG. 4

| PRIORITY (SELECTION) | GUIDE CONTENTS | PROCESSING (SELECTION) |
|---|---|---|
| LARGE | UPON TURNING TO RIGHT AND LEFT | SWITCHING: EMPHASIS CORRECTION |
| SMALL | UPON GOING STRAIGHT | AS IT IS |
| SMALL | UPON EXPLANATION OF FACILITIES | SWITCHING: NON-EMPHASIS CORRECTION |
| LARGE | UPON ARRIVAL AT DESTINATION | BEEP (LARGE) |
| LARGE | UPON JAMMING DETECTED | SWITCHING: EMPHASIS CORRECTION |
| LARGE | UPON EMERGENCY INFORMATION RECEIVED | MUTE |
| ⋮ | ⋮ | ⋮ |

FIG. 5

| PRESENT EMPHASIS CORRECTION PROCESS SIGNAL | ACOUSTIC GUIDE OF NAVIGATION SYSTEM | | HANDS-FREE DEVICE | TV SOUND |
|---|---|---|---|---|
| | PRIORITY SMALL | PRIORITY LARGE | | |
| ACOUSTIC GUIDE OF NAVIGATION SYSTEM | | | SWITCHING: EMPHASIS CORRECTION | UNCHANGED |
| HANDS-FREE DEVICE | ACCORDING TO TABLE IN FIG. 4 | | | UNCHANGED |
| TV SOUND | | | SWITCHING: EMPHASIS CORRECTION | |
| PRIORITY ORDER | 3 | 1 | 2 | 4 |

ACOUSTIC OUTPUT PROCESSING APPARATUS

BACKGROUND OF THE INVENTION

1. Field of the Invention

The present invention relates to an acoustic output processing apparatus for processing an acoustic output to be produced clearly by automatically selecting and correcting with emphasis a most important sound for a user from among various sounds produced within a room, such as the output of car audio, an acoustic guide for a car navigation system, and an acoustic output of a hands-free telephone. The invention also is capable of processing an acoustic output, including other acoustic output processing, corresponding to a priority order of various delivered sounds.

2. Description of the Related Art

Recently, acoustic guides are produced by various devices, and acoustic outputs are produced by various devices such as an audio system and TV. In vehicles in particular, acoustic guides are often provided by car navigation systems. Moreover, as mobile phones are becoming widespread, drivers frequently take them into vehicles so as to receive calls. Also, hands-free telephone devices are used for safer driving. In this case, sounds heard on the other end may be produced by an audio system in the vehicle other than an earphone and a speaker disposed close to a user.

Such an acoustic guide for a car navigation system is for guiding a driver to drive along a guidance route. It vocally performs guidance sequentially in various modes, especially for turning right or left at a crossing ahead while displaying route images on a screen. In order to enable a driver to follow a guidance route without needing to view the images, the acoustic guide is particularly important in the function of the navigation system.

Such an acoustic guide is produced while various kinds of noise enter a vehicle cabin and vary according to the vehicle travel state, such as an engine sound, wind noise, and a tire friction sound. There may sometimes be speaking voices of vehicle occupants, various kinds of music from an audio system, and radio news announcements while the acoustic guide is produced.

Furthermore, a TV monitor may sometimes be provided in a rear seat area and viewed by a vehicle owner or a family member. Therefore, within a cabin of a moving vehicle, with TV sound or telephone voices from a user or the other end of the hands-free phone, the acoustic guide of the navigation system may be produced.

In order to certainly convey the navigation acoustic guide to a user under such various kinds of noise and voices, it is preferable not to increase the power of the acoustic guide output needlessly, but it is preferable to adjust the sound volume corresponding to the state of the noise. In order to solve this problem, Japanese Unexamined Patent Application Publication No.11-166835, assigned to the same assignee as this application, discloses a navigation acoustic output correction device. In this device, on the basis of a sound pressure level of the navigation acoustic guide and a sound pressure level of ambient noise audible at a listening position, gain correction of the acoustic guide is performed.

According to the Publication mentioned above, noise components captured by a microphone disposed in the cabin are separated from the acoustic guide so as to obtain a sound pressure for each frequency band in advance, and the sound pressure gain for each frequency band of the navigation acoustic guide is obtained corresponding to the sound pressure of each noise, so that the sound pressure gain of the navigation acoustic guide is established based on this gain, enabling an appropriate sound pressure of the acoustic guide corresponding to the ambient noise to be obtained.

As described above, in a vehicle cabin, various acoustic output devices are used, and an acoustic guide is performed as needed as an important function of a car navigation system. By means of the technique described above, the acoustic guide can be performed with an appropriate sound pressure corresponding to acoustic outputs from surrounding devices or ambient noise; however, the target acoustic output to be clearly produced is only the navigation acoustic output, and the target acoustic output is separated from the other sounds in advance from among various sounds captured by the microphone disposed in the cabin.

The navigation acoustic output correction device described above is only effective for the navigation sounds established in advance. In order to clearly hear the voice of a hands-free device, for example, a circuit for separating the sound of the hands-free device from the other sounds and adjusting means for adjusting the sound gain of the hands-free device would need to be provided. With the other devices, similar means must be provided for clearly hearing them.

Providing a similar processing circuit for each device in such a manner wastefully complicates the configuration. Therefore, it is assumed the circuit is provided for a device desired by a user; however, there may be a large variety of user preferences, so that all of the preferences cannot be satisfied. Therefore, these demands cannot be satisfied by the technique described above.

Also, while the acoustic output of the hands-free device is being corrected with priority, when the guidance at an intersection to turn right or left is produced from the navigation system, the hands-free device assumes the acoustic guide output to be noise so as to produce its own output with a sound pressure larger than that of the acoustic guide output, so that the navigation acoustic guide cannot be heard and a driver may miss the guidance path.

Conversely, if the navigation acoustic guide is selected as the priority, and a comparatively unimportant guide such as the description of adjacent facilities is produced, if an important call is received by the hands-free device, the navigation system assumes the hands-free output to be noise so as to produce its own output clearly with a sound pressure to cancel the hands-fee output, so that the phone voice is scarcely heard.

As described above, there are a large variety of acoustic output devices in a vehicle cabin, such as an audio system, a hands-free device of a mobile phone, and a TV, each having a specific mode of operation. That is, in the audio system, a piece of favorite music may be heard as background music while canceling ambient noise so that it may be unimportant for users. The sound on the other end of the mobile phone produced by a speaker of the hands-free device may be frequently heard with concentrated attention as comparatively important voice for a user. Also, the TV sound is continuously produced so as to be unimportant; however there may be comparatively important information such as a news program.

Moreover, in the acoustic output of the navigation system, although it is especially important to guide a driver to turn right or left at an intersection as mentioned above, there are cases, in which the guidance for going straight is not so important; the description of facilities performed by the demand of a user does not create a problem even when being somewhat delayed; the guidance performed upon arrival at a destination is rather important so as to prevent a driver from going past; and the guidance informing a driver of congestion along the guidance path direction by a VICS (vehicle information and communication system) is comparatively important. Nevertheless, there are occasions when it is undesirable to give the navigation acoustic guide correction priority.

Even when there are provided a voice processing circuit for clearly listening to the navigation acoustic guide, a voice processing circuit for clearly listening to the acoustic output of a hands-free device, and further a voice processing circuit for clearly listening to a TV, when these acoustic outputs are overlapped, each correction is performed by increasing the source's sound pressure assuming the other sounds to be noise, resulting in an extremely undesirable situation.

As a countermeasure for the problems mentioned above, the acoustic output important for a user is designated in advance and the correction for clarifying this acoustic output is performed only when this acoustic output is to be produced. However, in this case, although it is responsive to various acoustic outputs, only the device selected by a user in advance performs emphasis correction for clarifying it, and other acoustic outputs cannot be corrected with emphasis.

Furthermore, as another countermeasure, while the audio system is being heard, noise outside is processed for elimination; a user selects to correct the navigation acoustic guide upon starting of important guidance; or the acoustic output of a hands-free device is switched to be clear upon receiving a mobile phone call, so that the acoustic output deemed most important is to be switched as needed on the audio device side. However, in this case, a user must select the device deemed most important, so that this operation is bothersome and undesirable especially for a driver for safety sake.

The above problem arises not only in a vehicle cabin but also in the home where an audio system and various acoustic guides of devices surrounding the audio system are widely used recently.

SUMMARY OF THE INVENTION

Accordingly, it is a principal object of the present invention to provide an acoustic output processing apparatus capable of processing acoustic output in various modes, such that in an audio system and various acoustic output devices, a device a user desires to clearly hear or an acoustic guide of the device deemed to be important is automatically selected so as to produce it clearly for the user while another acoustic output informs the user by a beep sound or by muting a specific sound when it is produced.

In order to solve the problems described above, an acoustic output processing apparatus according to the present invention comprises an acoustic correction filter for correcting with emphasis a specific sound among sounds delivered to the filter from a microphone; a selector having a correction output unit for delivering sounds received from an acoustic output device to the acoustic correction filter and a non-correction output unit for generating sounds received from an acoustic output device through a speaker without passing them through the acoustic correction filter, the selector delivering one of the received sounds from the correction output unit while delivering the other received sounds from the non-correction output unit; device operation-mode detecting means for detecting an operation mode of an acoustic output device and detecting a present mode of acoustic output processing; and an acoustic output processing control unit for performing operational control of acoustic output processing, including the control of the selector, by a factor corresponding to a result detected by the device operation-mode detecting means. Thereby, while acoustic outputs of an audio system and various acoustic output devices are being produced from the speaker, the acoustic output of a device a user particularly desires to hear clearly or an acoustic guide likely important in the device can be automatically selected, enabling the acoustic signal desired by the user to be clearly produced with emphasis.

Preferably, according to the present invention, the acoustic output processing control unit comprises a memory, in which modes of acoustic output processing are entered in advance, and the acoustic output-processing control unit performs operational control by reading data stored in the memory. Thereby, a user can record desirable modes of acoustic output processing in the memory in advance, so that the acoustic output processing control unit can perform various modes of acoustic output processing corresponding to the preference of the user by simply reading the memory.

Preferably, according to the present invention, the memory stores a priority order showing the degree of importance for a user, enabling the acoustic output processing control unit to correctly perform various kinds of acoustic output processing commencing with the selector switching control by a factor corresponding to the priority order.

Preferably, according to the present invention, the acoustic output processing control unit generates an audible notification such as a beep and simultaneously produces a display showing the beginning of a specific sound on a monitor screen when the acoustic signal not to be corrected is delivered. Thereby, even while correcting for a specific sound, the other sounds being scarcely heard, when a predetermined sound begins, a user can be prompted to look at the monitor screen by a beep.

Preferably, according to the present invention, the beep is generated with a plurality of modes corresponding to an operational mode of a device, so that while correcting for a specific sound, the other sounds being scarcely heard as mentioned above, when a predetermined sound begins, a user can be informed of it by the beep with the mode corresponding to its priority order, so as to change the degree of prompting to look at the monitor screen.

Preferably, according to the present invention, the acoustic output processing control unit makes the acoustic signal not to be corrected mute. Thereby, sounds that are not necessary for a user can be reduced in power, so that necessary sounds for the user can be clearly heard, even if the necessary sounds are not corrected with emphasis.

Preferably, according to the present invention, the acoustic output processing control unit changes a mode of acoustic output processing corresponding to a content of an acoustic guide of a navigation system. In the navigation system having various kinds of guides, the mode of acoustic output processing can be changed between guides important for a user and the others, enabling fine acoustic output processing to be performed to have a user-friendly acoustic output processing apparatus.

Preferably, according to the present invention, the acoustic output processing control unit performs a control operation of not entirely using the acoustic correction filter or a control operation of not switching the selector, corresponding to an operational mode of a device. Thereby, correction of a specific input sound, whereby the other sounds cannot be heard depending on the kind of sound, is not performed, so that the listener can hear them appropriately.

Preferably, according to the present invention, an audio signal is directly produced from a speaker without passing it through the selector. Thereby, the audio signal, which is generally lower in urgency and priority order than the other devices, can be distinguished as a signal not to be corrected with emphasis without a specific action such as switching.

Preferably, according to the present invention, an audio signal is directly produced from an audio speaker disposed in a vehicle, while other acoustic signals are produced from another speaker via the selector. Thus, while the audio signal, which is generally lower in urgency and priority order than the other devices, can be distinguished as a signal not to be corrected with emphasis without a specific action such as switching as mentioned above, the audio signal, to which most importance is attached in sound quality, can be independently produced from the audio speaker disposed in the vehicle, enabling desired sound quality to be maintained.

BRIEF DESCRIPTION OF THE DRAWINGS

FIG. 2 is a processing correspondence table upon signal interruption for use in performing various modes of acoustic output processing according to the embodiment;

FIG. 3 is a table showing the process contents of selectable items according to the embodiment;

FIG. 4 is a table showing an example of allocation by priority order of acoustic guides of a navigation system according to the embodiment;

FIG. 5 is a table showing an operative example of the processing correspondence table upon signal interruption according to the embodiment;

DESCRIPTION OF THE PREFERRED EMBODIMENTS

Figure 1:
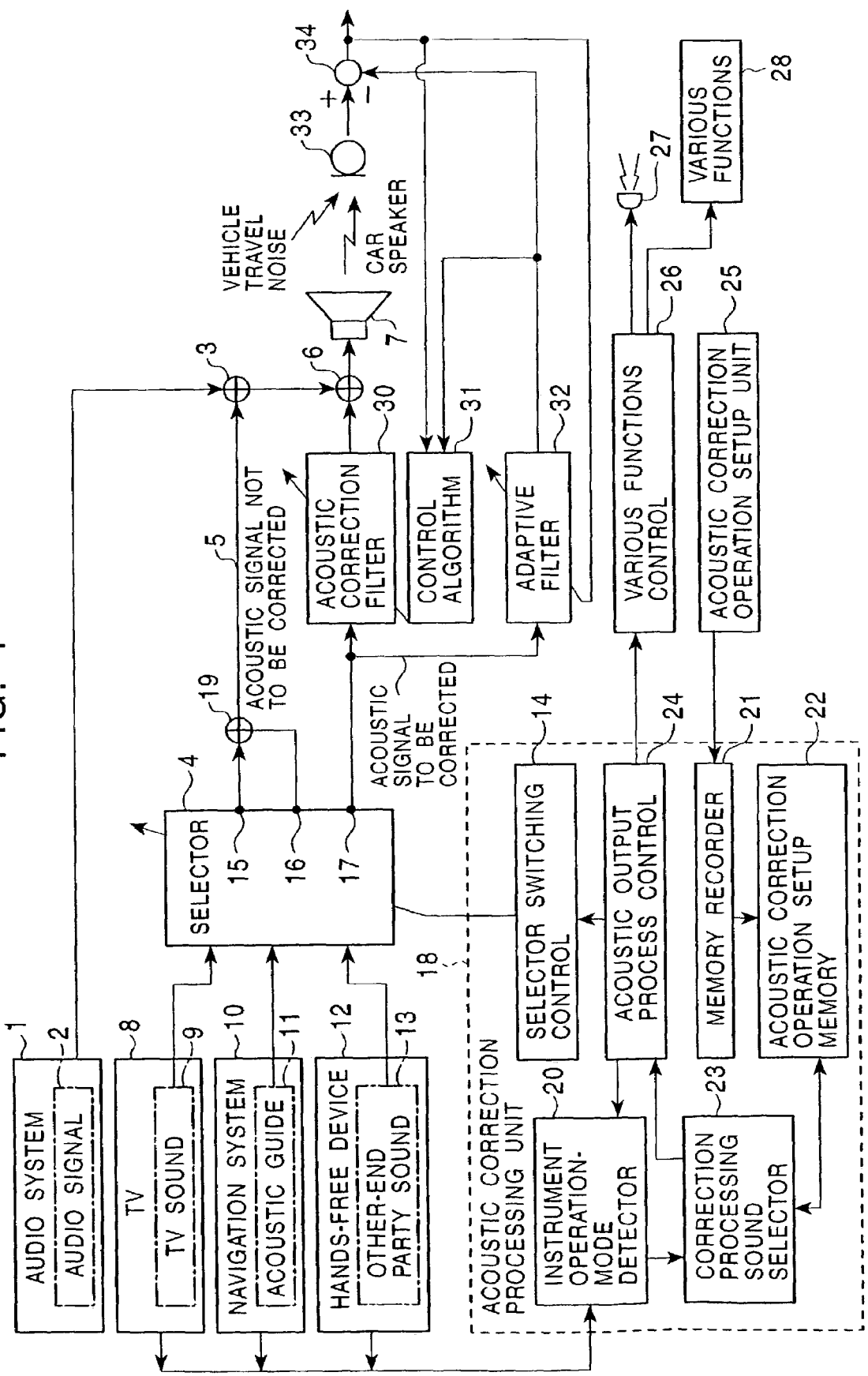
FIG. 1 is a functional block diagram of an embodiment of the present invention.

Embodiments of the present invention will be described with reference to the drawings. FIG. 1 is a functional block diagram of a first embodiment according to the present invention, specifically showing a configuration in which a speaker of an audio system disposed in a vehicle cabin is to produce the entire acoustic output such as the acoustic guide output of a navigation system, the acoustic output on the other end of a mobile phone from a hands-free device thereof, and the acoustic output of a TV.

Referring to FIG. 1, an audio signal 2 from an audio system 1 is mixed with an acoustic signal 5 selected by a selector 4 as a signal not to be corrected, which will be described later, at a first acoustic mixer 3, and the audio signal 2 is further mixed with an acoustic signal selected by the selector 4 as a signal to be corrected at a second acoustic mixer 6, and then is produced from a speaker 7 in the vehicle cabin as a sound or an audio sound. While the audio system 1 is not operating, only the acoustic signal not to be corrected 5 enters the first acoustic mixer 3 from the selector 4.

According to the embodiment shown in FIG. 1, the vehicle is provided with a TV 8 mounted therein so as to deliver a TV sound 9 to the selector 4, a navigation system 10 mounted therein for delivering various acoustic guides 11 to the selector 4, and a hands-free device 12 mounted therein for delivering sounds 13 on the other end of a mobile phone connected thereto to the selector 4. These acoustic signals delivered to the selector 4 are divided into one acoustic signal, which is acoustically corrected and produced with emphasis, and the other acoustic signals.

According to the embodiment shown in the drawing, the acoustic signal selected in the selector 4 to be acoustically corrected enters an acoustic correction filter 30 to be acoustically corrected (as will be described) from a correction-process output terminal 17. Then, it is delivered to the second acoustic mixer 6 and clearly produced from the speaker 7 in the vehicle cabin. The other acoustic signals not selected to be corrected are delivered from a first non-correction process output terminal 15 and a second non-correction process output terminal 16 and mixed with each other in a third acoustic mixer 19. Then, after being mixed with the audio signal in the first acoustic mixer 3, they are mixed with the signal acoustically corrected as mentioned above in the second acoustic mixer 6 and produced from the speaker 7 in the vehicle cabin. However, they are attenuated relative to the corrected signal, so that a user may scarcely hear them.

In the apparatus, although it is possible to set the TV sound 9 to be corrected, since it is scarcely necessary to do so, it may always be established not to be corrected. In that case, the TV sound 9 is always connected to the first non-correction process output terminal 15. Any one of the acoustic guide 11 of the navigation system 10 and the sound 13 on the other end of the hands-free device 12 is selected and connected to the correction-process output terminal 17 of the selector 4 while the other is connected to the second non-correction process output terminal 16. If the vehicle has various optional devices to be connected to the speaker 7, the outputs thereof are all delivered to the selector 4 and are provided with respective non-correction process output terminals for each of these devices.

An acoustic correction processing unit 18 including a selector switching control 14 is provided with a device or instrument operation-mode detector 20, in which various operating signals of each device are delivered while a signal of an acoustic output process control 24 performing acoustic output processing is delivered. When the operating state of the navigation system 10 is detected, the device operation-mode detector 20 can detect whether the state of the acoustic guide produced from the navigation system 10 is an important guide such as a guide at an intersection for turning right or left, or a non-urgent guide such as the guide of facility information.

When the hands-free device 12 receives a telephone call, the acoustic correction processing can be performed instantly by detecting the call by the device operation-mode detector 20 so as to determine the priority order of the call before it is produced. When an interrupting signal for acoustic output processing is produced from each device, the operation of the device can be detected by receiving the interrupting signal.

The acoustic correction processing unit 18 is connected to an acoustic correction operation setup unit 25 so as to perform acoustic correction processing and the operations related thereto with various modes according to a user's preference as will be described later. For example, a user can enter various settings by operating a remote controller so as to respond to prompts that are displayed on a monitor screen. The data established in the acoustic correction operation setup unit 25 is delivered to a memory recorder 21 and stored in an acoustic correction operation setup memory 22.

In a correction processing sound selector 23 of the acoustic correction processing unit 18, a presently operating device detected by the device operation-mode detector 20 and an acoustic output process operation corresponding to the operation presently controlled by the acoustic output process control 24 are read from the acoustic correction operation setup memory 22 and delivered to the acoustic output process control 24. In the acoustic output process control 24, a signal is delivered to the selector switching control 14 corresponding to the operation stored in the acoustic correction operation setup memory 22 so as to perform the selecting operation of the selector 4. The acoustic output process control 24 also controls various functions 28 necessary for operational control of the acoustic output apparatus while delivering a control signal to a various-functions control 26 for operating a buzzer 27 generating a beep.

An acoustic signal selected by the selector 4 for performing the acoustic correction process enters the acoustic correction filter 30 from the correction-process output terminal 17. The acoustic signal is corrected by the acoustic correction filter 30, which is adjusted according to a control algorithm 31 based on a loudness compensation principle, for example, and is mixed with another acoustic signal in the second acoustic mixer 6 so as to generate an output in the vehicle cabin from the speaker 7.

The sound from the speaker 7 is captured by a microphone 33, and from the signal delivered by the microphone 33, the acoustic signal selected to be corrected by the selector 4 is further adjusted by an adaptive filter 32 and is subtracted in a subtractor 34. The subtractive difference enters the control algorithm 31 of the acoustic correction filter 30 so as to form a more appropriate acoustic correction filter 30. The subtractive difference produced in the subtractor 34 is also delivered to the adaptive filter 32 for obtaining more approximate signal adjusting data so as to become a signal corresponding to the subtractor 34, and is further delivered to the control algorithm 31 so as to make the acoustic correction filter 30 more appropriate. The above-mentioned means for processing acoustic correction is shown as an example, and other known means, such as Japanese Unexamined Patent Application Publication No. 11-166835 assigned to the same assignee as this application, may be adopted.

The acoustic correction operation setup memory 22 shown in FIG. 1 can record various kinds of acoustic correction process operations with various modes. For example, the memory 22 can record by appropriately selecting and entering the corresponding item in the table of FIG. 2. The table of FIG. 2 is for determining an operation and is composed of a vertical column constituting items of "present emphasis correction process signals" and priority order and a horizontal row constituting items of "interruption signals", which are produced by new devices operated thereafter so as to generate an output.

In the table of FIG. 2, as the items of the present emphasis correction process signals, there are "an acoustic guide of a navigation system", "a hands-free telephone", and "a TV sound", signals of which are delivered in the selector 4 shown in FIG. 1. As for the interruption signals, especially for the navigation acoustic guide shown in the vertical column, the priority thereof is divided into "priority small" and "priority large" according to the kind of acoustic guide. While the guide sound is produced as the present correction process signal, when the hands-free device begins operating, the operation thereof is to be a "selected item (1)", and when the TV sound begins operating, the operation thereof is to be a "selected item (2)". Similarly, "selected items (3) to (8)" are allocated corresponding to items of the vertical column and the horizontal row. These selected items are arbitrarily selected and set from the process contents shown in FIG. 3. Also, "priority orders (1) to (4)" are allocated corresponding to the kind of interruption signal, so that when a plurality of interruption signals enter simultaneously, the correction processing is smoothly performed as requested.

As process contents of selectable items shown in FIG. 3, six modes of "switching: emphasis correction", "switching: non-emphasis correction", "beep (small)", "beep (large)", "mute", and "unchanged" are prepared. If the "switching: emphasis correction" is selected, the correction processing of the interrupted acoustic signal is selected and performed with priority so as to produce with emphasis the output of this acoustic signal. At this time, the acoustic correction device is turned ON so as to switch the control-target signal by the selector.

If the "switching: non-emphasis correction" is selected, the interrupted signal is selected with priority, but the correction is not performed. At this time, the acoustic correction device is turned OFF. If the "beep (small)" is selected, a small beep is produced by a buzzer 27 so as to prompt a user to look at a monitor. Also, if the "beep (large)" is selected, a large beep is produced by the buzzer 27 so as to powerfully prompt a user to look at the monitor.

Other than the large and small beep, various modes of beep differentiation may be incorporated, such as the differentiation between continuous and discontinuous sounds, between various modes of discontinuous sounds, and between various tones. While the beep is produced, even if the interrupted signal is delivered, the acoustic processing is unchanged and performed. If "mute" is selected, the audio system is muted so as to emphasize other sounds relatively. Also, if "unchanged" is selected, the present output is produced from the speaker as it is, so that the interruption is not allowed.

On the other hand, in the items of the navigation acoustic guide in the processing correspondence table upon signal interruption of FIG. 2, the allocation between high-priority order and low-priority order is performed according to the table of FIG. 4. That is, if the acoustic guide is for turning right or left, the priority order is selected to be "large" so that the interruption of this signal is selected with priority so as to switch the control-target signal by the selector and to perform the correction processing. If the acoustic guide is for proceeding straight, the priority order is selected to be "small" so that the above switching processing and correction processing is not performed. If the acoustic guide is for guiding facilities, the priority order is selected to be "small" in the same way as for proceeding straight, but switching the control-target signal by the selector is performed while the correction processing is not performed.

If the navigation acoustic guide is for guiding upon arrival at a destination, the priority order is selected to be "large" so as not to pass the destination by mistake; and processing to prompt a user to look at a monitor screen is performed with the large beep. If the guide is to advise of congestion detected with the VICS, the priority order is selected to be "large" so as to switch the control-target signal by the selector and to perform the correction processing. Furthermore, if the guide is to advise of receiving emergency information obtained with the VICS, the priority order is selected to be "large" so as to mute the other acoustic signal outputs. The selectable items shown in FIGS. 3 and 4 are only examples; alternatively, other various modes of set-up may be adopted.

Examples of items and priority order selected from the table of FIG. 2, which is set as described above, are shown in the table of FIG. 5. In the examples, while the present navigation acoustic guide is corrected with emphasis, if the interruption signal is delivered from the hands-free device, the control-target signal is switched by the selector and the correction processing of this sound is performed. Also, if the interruption signal is delivered from the TV sound, the processing is not changed. On the other hand, while the hands-free device is presently operated and the acoustic output on the other end is corrected and produced from the speaker, if the interruption acoustic guide signal is delivered from the navigation system, the processing is performed according to the table of FIG. 4. It is the same as above when the interruption acoustic guide signal is delivered from the navigation system while the TV sound is corrected with emphasis.

Also, while the hands-free device is being operated and the acoustic output on the other end is corrected and produced from the speaker as described above, if the interruption signal is delivered from the TV sound output, the processing is not changed. Also, while the TV sound is corrected, if the interruption signal is delivered from the hands-free device, the control-target signal is switched by the selector and the correction processing of this sound is performed.

In the priority order of these various sounds, the priority order (1) is given to the navigation acoustic guides established to be the large priority in the table of FIG. 4 in the acoustic guides from the navigation system; the priority order (2) is given to the acoustic output on the other end of the hands-free device; the priority order (3) is given to the navigation acoustic guides established to be the small priority in the table of FIG. 4 in the acoustic guides from the navigation system; and the lowest priority order (4) is given to the TV sound. Since these settings may be different for each user, even in the settings as above, it is preferable to be allowed to instantly return to a predetermined default state by resetting.

Figure 6:
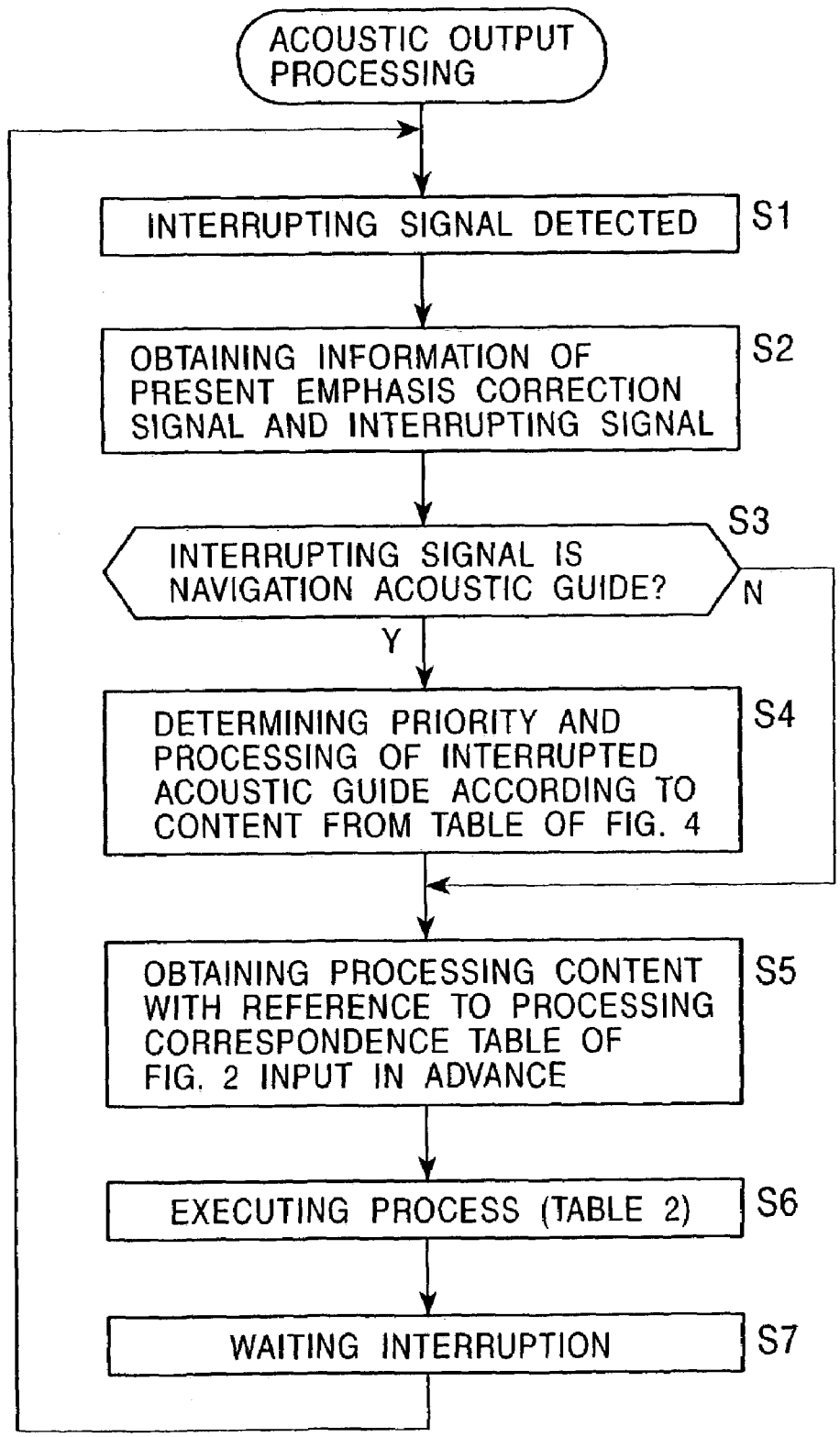
FIG. 6 is an operational flowchart of the embodiment.

The acoustic output correction apparatus performing under conditions established as shown in the tables with the functional configuration described above can be sequentially operated according to the operational flow shown in FIG. 6. That is, in the acoustic output processing shown in FIG. 6, the operation is started by detecting the interrupting signal to be acoustically processed generated by the operation of a device (step S1), and then, the information of the present correction signal and the interrupting signal is obtained (step S2). These are performed by detecting the state of each device in the device operation-mode detector 20 shown in FIG. 1 and by detecting various kinds of processing in the acoustic output process control 24 as well.

Then, it is determined whether the interrupting signal is the navigation acoustic guide or not (step S3). If it is determined to be the acoustic guide, the priority order and its process content are determined from the table of FIG. 4 corresponding to the content of the interrupted acoustic guide (step S4). After step S4 or when the interrupting signal is determined not to be the navigation acoustic guide at step S3, the process content is obtained with reference to the processing correspondence table of FIG. 2 storing the user's preference data (step S5). Then, processing is executed according to the processing content of the table of FIG. 2 (step S6). Thereafter, the process is placed in the wait state (step S7) and returned to step S1 to await the detection of the interrupting signal so as to repeat the above-mentioned sequences.

Figure 7:
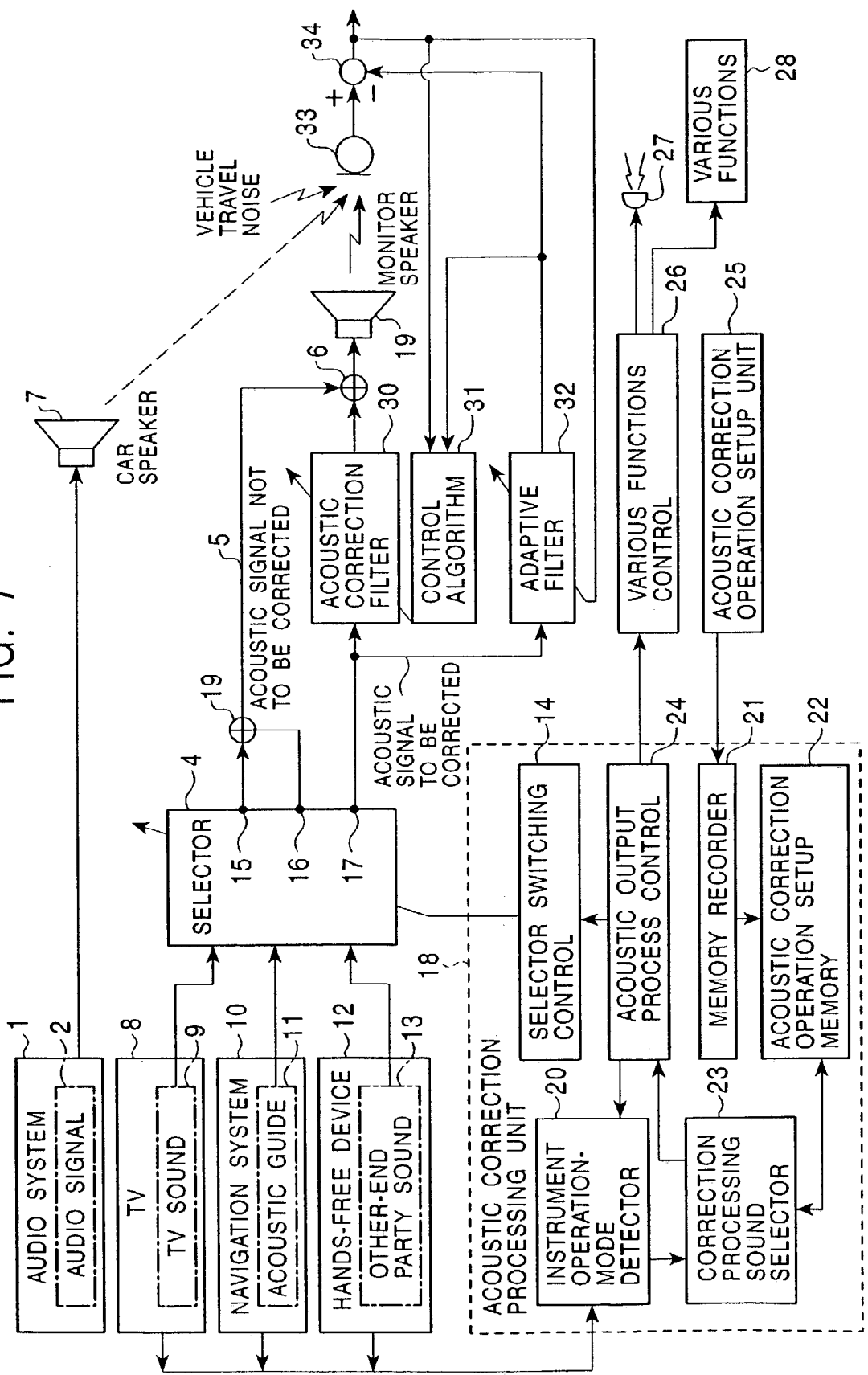
FIG. 7 is a functional block diagram of another embodiment of the present invention.

According to the embodiment shown in FIG. 1, from the speaker 7 delivering the output of the audio system 1, acoustic signals of various devices are mixed and delivered. Additionally, as shown in FIG. 7, while the audio signal 2 is produced from the speaker 7, the system may also be configured to produce the acoustic signals of other devices from a monitor speaker 19. In this case, the processing may be operated in substantially the same way as in the above-described embodiment; however, features different from FIG. 1 are that the first mixer 3 is not used, and the audio acoustic output of the speaker 7, the acoustic output of the monitor speaker 19, and vehicle travel noise are delivered to the microphone 33.

According to the present invention, even when various devices other than those shown in the embodiment described above are connected to the acoustic output apparatus, the processing can be performed with the same mode described above. Also, as one of various modes of the acoustic output processing, comparatively important sounds being scarcely heard by the above-described correction may be notified to a user by flashing or a warning display on the display screen rather than with a beep.

The invention claimed is:

1. An acoustic output processing apparatus comprising:
   an acoustic correction filter for correcting with emphasis a specific sound among sounds produced within a space;
   a selector having a correction output unit for delivering sounds received from an acoustic output device to the acoustic correction filter and a non-correction output unit for generating sounds received from an acoustic output device through a speaker without passing them through the acoustic correction filter, the selector delivering one of the received sounds through the correction output unit while delivering the other received sounds through the non-correction output unit;
   device operation-mode detecting means for detecting an operation mode of an acoustic output device and detecting a present mode of acoustic output processing; and
   an acoustic output processing control unit for performing operational control of acoustic output processing, including the control of the selector, by a factor corresponding to a result detected by the device operation-mode detecting means.

2. An apparatus according to claim 1, wherein the acoustic output processing control unit comprises a memory in which modes of acoustic output processing are stored in advance, and the acoustic output processing control unit performs operational control by reading data stored in the memory.

3. An apparatus according to claim 2, wherein the memory stores priority order showing the degree of importance for a user.

4. An apparatus according to claim 1, wherein the acoustic output processing control unit generates an audible notice when the acoustic signal not to be corrected is delivered.

5. An apparatus according to claim 4, wherein the audible notice is generated in a plurality of modes corresponding to an operational mode of a device.

6. An apparatus according to claim 1, wherein the acoustic output processing control unit mutes the acoustic signal not to be corrected.

7. An apparatus according to claim 1, wherein the acoustic output processing control unit changes a mode of acoustic output processing by a factor corresponding to the content of an acoustic guide of a navigation system.

8. An apparatus according to claim 1, wherein the acoustic output processing control unit is performed without one of using the acoustic correction filter and switching the selector entirely, by a factor corresponding to an operational mode of a device.

9. An apparatus according to claim 1, wherein an audio signal is directly produced from a speaker without being delivered by the selector.

10. An apparatus according to claim 1, wherein an audio signal is produced from an audio speaker disposed in a vehicle, while the other acoustic signals are produced from another speaker through the selector.

11. An acoustic output processing apparatus comprising:
an acoustic correction filter for correcting with emphasis a specific sound among sounds produced within a space;
a selector having a correction output unit for delivering sounds received from an acoustic output device to the acoustic correction filter and a non-correction output unit for generating sounds received from an acoustic output device through a speaker without passing them through the acoustic correction filter, the selector delivering one of the received sounds through the correction output unit while delivering the other received sounds through the non-correction output unit;
device operation-mode detecting means for detecting an operation mode of an acoustic output device and detecting a present mode of acoustic output processing; and
an acoustic output processing control unit for controlling the selector according to a result detected by the device operation-mode detecting means so as to select a received signal with large priority order reflecting the degree of importance for a user and produce it through the correction output unit.

12. An apparatus according to claim 11, wherein the acoustic output processing control unit generates an audible notice when the acoustic signal not to be corrected is delivered.

13. An apparatus according to claim 12, wherein the audible notice is generated in a plurality of modes corresponding to an operational mode of a device.

14. An acoustic output processing method comprising:
detecting the operation of an acoustic output device and a present operational mode of acoustic output processing;
controlling the acoustic output processing corresponding to a detected result;
specifying a predetermined sound included among sounds produced within a space based on the control of the acoustic output processing; and
correcting with emphasis the specified sound with an acoustic correction filter;
wherein the predetermined sound is specified from among the sounds produced in the space according to the priority of the sounds indicating the degree of importance for a user; and
wherein the act of controlling the acoustic output processing is performed by changing a mode of acoustic output processing according to the content of an acoustic guide of a navigation system.

15. A method according to claim 14, wherein the act of controlling the acoustic output processing is performed by reading data stored in a memory, in which modes of the acoustic output processing are stored in advance.

16. A method according to claim 14, wherein the act of controlling the acoustic output processing is performed by generating an audible notice when an acoustic signal not to be corrected is delivered.

17. A method according to claim 16, wherein the audible notice is generated in a plurality of modes corresponding to an operational mode of a device.

18. A method according to claim 14, wherein the act of controlling the acoustic output processing is performed by muting the acoustic signal not to be corrected.

19. A method according to claim 14, wherein the act of controlling the acoustic output processing is performed without using the acoustic correction filter entirely by a factor corresponding to an operational mode of a device.

* * * * *